United States Patent
Zhao

(10) Patent No.: US 10,208,057 B2
(45) Date of Patent: Feb. 19, 2019

(54) NUCLEATOR COMPOSITION COMPRISING SORBITOL ACETAL, SORBITOL DIACETAL AND SORBITOL TRIACETAL

(71) Applicant: GCH TECHNOLOGY CO., LTD., Guangzhou (CN)

(72) Inventor: Wenlin Zhao, Guangzhou (CN)

(73) Assignee: GCH Technology Co., Ltd., Guangzhou (CN)

( * ) Notice: Subject to any disclaimer, the term of this patent is extended or adjusted under 35 U.S.C. 154(b) by 37 days.

(21) Appl. No.: 15/542,818

(22) PCT Filed: Sep. 5, 2016

(86) PCT No.: PCT/CN2016/098059
§ 371 (c)(1),
(2) Date: Jul. 11, 2017

(87) PCT Pub. No.: WO2018/040093
PCT Pub. Date: Mar. 8, 2018

(65) Prior Publication Data
US 2018/0273545 A1  Sep. 27, 2018

(51) Int. Cl.
*C07D 493/04* (2006.01)
*C08K 5/07* (2006.01)
*C08L 23/06* (2006.01)
*C08L 23/12* (2006.01)
*C07D 319/06* (2006.01)
*C08J 5/18* (2006.01)
*C08J 3/20* (2006.01)
*C08K 5/1565* (2006.01)
*C08K 5/1575* (2006.01)

(52) U.S. Cl.
CPC ......... *C07D 493/04* (2013.01); *C07D 319/06* (2013.01); *C08J 3/203* (2013.01); *C08J 5/18* (2013.01); *C08K 5/07* (2013.01); *C08K 5/1565* (2013.01); *C08K 5/1575* (2013.01); *C08L 23/06* (2013.01); *C08L 23/12* (2013.01); *C08J 2323/06* (2013.01); *C08J 2323/12* (2013.01); *C08K 2201/014* (2013.01)

(58) Field of Classification Search
CPC ...... C07D 493/04; C07D 319/06; C08K 5/07; C08K 5/1565; C08K 5/1575; C08K 2201/014; C08L 23/06; C08L 23/12; C08J 3/203; C08J 5/18; C08J 2323/06; C08J 2323/12

USPC .......................................................... 524/108
See application file for complete search history.

(56) References Cited

U.S. PATENT DOCUMENTS

| | | | | |
|---|---|---|---|---|
| 5,216,051 A | * | 6/1993 | Smith ................. | C07D 493/04 524/108 |
| 6,245,813 B1 | * | 6/2001 | Zhou .................... | A61K 31/198 514/563 |
| 6,245,843 B1 | * | 6/2001 | Kobayashi ........... | C07D 493/04 524/109 |

FOREIGN PATENT DOCUMENTS

| | | | |
|---|---|---|---|
| CN | 1241190 A | | 1/2000 |
| CN | 1563012 A | | 1/2005 |
| CN | 101434606 A | | 5/2009 |
| CN | 101987891 A | * | 3/2011 |
| CN | 101987891 A | | 3/2011 |
| CN | 102675331 A | * | 9/2012 |
| CN | 102675331 A | | 9/2012 |
| CN | 105623105 A | | 6/2016 |

OTHER PUBLICATIONS

CN 102675331A, 2000, English Abstract from EspaceNet.
CN 102675331A, 2000, English translation of Description from EspaceNet.
CN 101987891A, 2011, English Abstract from EspaceNet.
CN 101987891A, 2011, English translation of Description from EspaceNet.
CN 105623105A, 2016, English Abstract from EspaceNet.
CN 105623105A, 2016, English translation of Description from EspaceNet.
International Search Report of PCT/CN2016/098059, translated, dated May 23, 2017.
CN 1563012A, 2005, English Abstract from EspaceNet.
CN 101434606A, 2009, English Abstract from EspaceNet.
CN 101434606A, 2009, English translation of Description from EspaceNet.
CN 101434606A, 2009, English translation of Claims from EspaceNet.

* cited by examiner

*Primary Examiner* — Michael Bernshteyn
(74) *Attorney, Agent, or Firm* — Liang & Frank LLP

(57) ABSTRACT

The present invention provides a nucleator composition comprising sorbitol acetal, sorbitol diacetal, and sorbitol triacetal. The nucleator composition can improve the nucleation performance of a polymer, increase transparency, glossiness, flexural modulus and tensile strength of polymer films, polymer sheets and polymer molding articles, and increase heat distortion temperature and dimensional stability of polymer articles.

29 Claims, No Drawings

NUCLEATOR COMPOSITION COMPRISING SORBITOL ACETAL, SORBITOL DIACETAL AND SORBITOL TRIACETAL

CROSS REFERENCE TO RELATED APPLICATION

The present application is a U.S. national phase of international application, No. PCT/CN2016/098059, filed on Sep. 5, 2016, the disclosures of which are hereby incorporated by reference.

FIELD OF THE INVENTION

The present invention is generally related to nucleators useful for the preparation of polymers and uses thereof, and more particularly, to a nucleator composition comprising sorbitol triacetal, sorbitol diacetal, and sorbitol acetal, and a method for preparing the same.

BACKGROUND OF THE INVENTION

At present, sorbitol diacetal is generally used as a basic ingredient of a sorbitol nucleator used industrially. Sorbitol acetal and sorbitol triacetal are needed to be removed from the sorbitol nucleator as impurities. Alternatively, the reaction condition of a preparation process of sorbitol diacetal needs to be controlled, so as to avoid generating sorbitol acetal and triacetal. For instance, Chinese patent application, CN 200410026622.8, discloses a method for purifying nucleators, in which methylene benzylidene sorbitol and trimethylene benzylidene sorbitol are removed to improve the purity of the nucleator. However, in CN 200410026622.8, the purity of the purified nucleator cannot reach 100% yet, and the impurities and concentrations thereof in the nucleator cannot be determined.

Other sorbitol nucleators may contain too much triacetal or contain no triacetal. For instance, Chinese patent application CN 200810219978.1 discloses a method for preparing nucleators. During the preparation of the nucleator, the amount of aromatic aldehyde added, the reaction time and reaction temperature are controlled. Because no special attention has been paid to the order of addition, triacetal and diacetal in the products cannot be controlled precisely. Moreover, effects of particular concentrations of triacetal in the nucleator on the performances of the products have not been studied.

DESCRIPTION OF THE INVENTION

One object of the present invention is to provide a nucleator composition containing certain amounts, described below, of sorbitol acetal, sorbitol diacetal and sorbitol triacetal. The nucleator composition can improve nucleation performance of polymers. In addition, effects of various concentrations of sorbitol triacetal and sorbitol acetal of the nucleator composition on various nucleation of polymers have also been studied.

The word "nucleator" used herein, refers to a nucleating agent, which is used for the nucleation of a polymer.

In the first aspect, the invention provides a nucleator composition, comprising a compound represented by formula (I), a compound represented by formula (II), a compound represented by formula (III), and a compound represented by formula (IV),

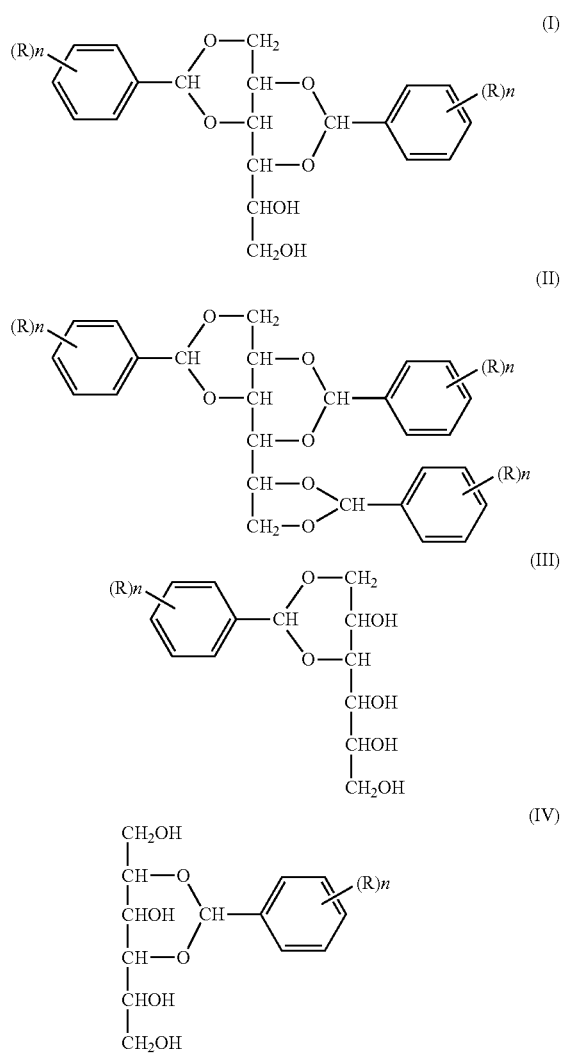

wherein each of the n in formulae (I), (II), (III) and (IV) is independently 1 or 2;

R is selected from $C_1$-$C_8$ alkyl, $C_1$-$C_4$ alkoxy, carboxy, hydroxyl, halogen, and $C_1$-$C_6$ alkylthio;

and the ratio of the weight of the compound represented by formula (I), the weight of the compound represented by formula (II), and the combined weight of the compounds represented by formula (III) and formula (IV) is (97.00-99.90):(0.20-8.00):(0.02-1.00).

Preferably, the ratio of the weight of the compound represented by formula (I), the weight of the compound represented by formula (II), and the combined weight of the compounds represented by formula (III) and formula (IV) is (97.00-99.90): (0.20-5.00): (0.02-0.80).

Preferably, the ratio of the weight of the compound represented by formula (I), the weight of the compound represented by formula (II), and the combined weight of the compounds represented by formula (III) and formula (IV) is (97.00-99.90): (0.20-3.00): (0.02-0.15).

Preferably, R is —Cl, —Br, —$CH_3$ or —$CH_2$—$CH_3$.

One of the embodiments of the invention provides a nucleator composition consisting of a compound represented by formula (I), a compound represented by formula (II), a compound represented by formula (III), and a compound represented by formula (IV) as defined above.

Preferably, the compound represented by formula (I) may be referred to as sorbitol diacetal, the compound represented by formula (II) may be referred to as sorbitol triacetal, and the compounds represented by formulae (III) and (IV) may be individually referred to as sorbitol acetal.

In the second aspect, the invention provides a method for preparing the nucleator composition of the invention, comprising the steps of: 1) mixing ⅓ by weight of an aromatic aldehyde needed and all sorbitol in a vessel by stirring to form a mixture;

2) adding cyclohexane to the mixture of step 1);

3) adding a composite catalyst to the product of step 2);

4) heating the product of step 3) for cyclohexane refluxing to carry out dehydration condensation reaction, then continuous heating for 0.4-1.0 hour;

5) adding cyclohexane and ⅓ by weight of the aromatic aldehyde needed to the product of step 4);

6) heating the product of step 5) for 0.4-1 hour to form a heated mixture;

7) adding cyclohexane and ⅓ by weight of the aromatic aldehyde needed to the heated mixture, and keeping heating until the mole ratio of water to sorbitol collected in an oil-water separator is 1.5-2:1;

8) lowering the temperature, reducing the pressure inside the vessel and recovering cyclohexane and water via distillation, and then obtaining a crude product;

9) dispersing the crude product into water, adding sodium hydroxide and hydrogen peroxide, and stirring; and 10) filter pressing, washing, and drying, and then obtaining a white powder of the nucleator composition, wherein the aromatic aldehyde is represented by the following formula

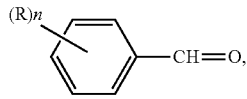

wherein n is 1 or 2, and R is selected from $C_1$-$C_8$ alkyl, $C_1$-$C_4$ alkoxy, carboxy, hydroxyl, halogen, or $C_1$-$C_6$ alkylthio, and the composite catalyst comprises a mixture of toluene-p-sulfonic acid and glycol ether.

In the alternative method of the second aspect of the present invention, the volume ratio of cyclohexane added in step 5) to cyclohexane in step 1) can optionally be 1:3, the volume ratio of cyclohexane added in step 7) to cyclohexane in step 1) can optionally be 1:3, and the weight of cyclohexane added in step 5) can optionally be equal to the weight of cyclohexane added in step 7).

Preferably, the aromatic aldehyde is chlorobenzaldehyde, bromobenzaldehyde, methylbenzaldehyde, p-ethyl benzaldehyde, 3,4-dimethylbenzaldehyde, 3,4-diethyl benzaldehyde, 3,4-dichlorobenzaldehyde, or 3,4-dibromobenzaldehyde.

In a preferable method of the second aspect of the present invention, the composite catalyst includes a mixture of toluene-p-sulfonic acid and glycol ether. Preferably, the alcohol ether is ethylene glycol monomethyl ether, ethylene glycol dimethyl ether, ethylene glycol diethyl ether, ethylene glycol monobutyl ether or ethylene glycol di-butyl ether. Also preferably, the mole ratio of toluene-p-sulfonic acid to alcohol ether is 3-5:8-10.

In the third aspect, the invention provides a use of the nucleator composition of the invention in the preparation of a polymer with improved performance, wherein the polymer is polyethylene or polypropylene, and the performance includes one or more of reduction of extrusion temperature, improvement of transparency, glossiness, flexural modulus and/or tensile strength of polymer films, polymer sheets and polymer moulding articles, improvement of heat distortion temperature and/or dimensional stability of polymer articles, reduction of molding cycle, and improvement of production efficiency.

Alternatively the invention is directed to a use of the nucleator composition of the invention in the preparation of a polymer with improved performance, wherein the polymer is polyethylene or polypropylene, and the improved performance includes one or more of (a) reduction of extrusion temperature, (b) increase of transparency, (c) increase of glossiness, (d) improvement of flexural modulus, (e) improvement of tensile strength, (f) improvement of heat distortion temperature, (g) improvement of dimensional stability, (h) reduction of the number of molding cycle, and (i) improvement of efficiency of production of the polymer.

Preferably, in the use of the nucleator composition of the invention to prepare a polymer with improved performance, the polymer prepared has improved transparency and/or reduced extrusion temperature.

Preferably, the improved polymer can be in the form of a polymer film, polymer sheet, polymer moulding article or polymer article.

Also provided is a method for preparing a polymer with improved performance, comprising a nucleation step of adding the nucleator composition of the invention to a polymer, wherein the polymer is polyethylene or polypropylene, and the performance includes one or more of reduction of extrusion temperature, improvement of transparency, glossiness, flexural modulus and/or tensile strength of polymer films, polymer sheets and polymer moulding articles, improvement of heat distortion temperature and/or dimensional stability of polymer articles, reduction of molding cycle, and improvement of production efficiency.

The invention also provides a method of preparing an improved polymer, comprising adding the nucleator composition of the invention to a starting polymer without the nucleator composition of the invention to obtain the improved polymer, wherein the polymer is polyethylene or polypropylene, and wherein the improved polymer has at least one improved performance including one or more of (a) reduced extrusion temperature, (b) increased transparency, (c) increased glossiness, (d) increased flexural modulus, (e) increased tensile strength, (f) improvement of heat distortion temperature, (g) improvement of dimensional stability, (h) reduction of the number of molding cycle, and (i) increased efficiency of production of the polymer, compared with the starting polymer without the nucleator composition of the invention.

Preferably, in the method, the improved performance can be increased transparency and/or reduced extrusion temperature.

Optionally, in the method, the improved polymer can be in the form of a polymer film, polymer sheet, polymer moulding article or polymer article. In some of the embodiments of the method, the improved polymer can be in the form of a polymer film, polymer sheet, or polymer moulding article, and the improved performance can be increased flexural modulus and tensile strength of the polymer film, polymer sheet, or polymer moulding article. In the method, optionally the improved polymer can be in the form of a polymer article, and the improved performance can be increased heat distortion temperature and/or improved dimensional stability.

Also provided is a method for preparing a polymer with improved transparency and reduced extrusion temperature, comprising a nucleation step of adding the nucleator composition of the invention to the polymer.

Preferably the polymer is polyethylene or polypropylene.

In the fourth aspect, the invention provides a polymer composition comprising a polymer and the nucleator composition of the present invention, wherein the weight content of the nucleator composition in the composition can be about 0.03-0.3%. Preferably the weight content of the nucleator composition in the polymer composition can be about 0.05-0.25%. Also preferably the polymer is polyethylene or polypropylene.

Furthermore, in the present invention, the polyethylene can optionally be low density polyethylene, medium density polyethylene, high density polyethylene, linear low density polyethylene, ultrahigh molecular weight polyethylene, and/or ethylene copolymer. Preferably the ethylene copolymer is one of ethylene-propylene copolymer, EVA, ethylene-butene copolymer, ethylene-octene copolymer, and ethylene unsaturated ester copolymer.

Furthermore, in the present invention, the polypropylene can be one of isotactic polypropylene, random polypropylene, syndiotactic polypropylene, chlorinated polypropylene, and grafted polypropylene.

The nucleator composition of the present invention can remarkably improve performances of polyethylene (PE) and polypropylene (PP), and especially can reduce the processing temperatures of PE and PP. Compared with a nucleator containing sorbitol diacetal but no sorbitol acetal or sorbitol triacetal, the nucleator composition of the invention containing sorbitol diacetal, sorbitol acetal and sorbitol triacetal can reduce the extrusion temperature (for instance, by more than 10° C.) and reduce the energy consumption in the processing procedure. Moreover, the nucleator composition of the present invention have unexpected effects of improving polymers' performances including improvement of transparency, glossiness, flexural modulus and/or tensile strength of polymer films, polymer sheets and polymer moulding articles, and improvement of heat distortion temperature and/or dimensional stability of polymer articles.

EXAMPLES

The composite catalysts used in the examples of the present invention mainly included:

Composite catalyst 1 which comprised toluene sulphonatic acid and ethylene glycol monomethyl ether, and the mole ratio of the toluene sulphonatic acid to the ethylene glycol monomethyl ether was 3:10;

Composite catalyst 2 which comprised toluene sulphonatic acid and ethylene glycol dimethyl ether, and the mole ratio of the toluene sulphonatic acid to the ethylene glycol dimethyl ether was 3:10; or Composite catalyst 3 which comprised benzenesulfonic acid, ethylene glycol di-butyl ether and Span-40, and the mole ratio of benzenesulfonic acid, ethylene glycol di-butyl ether and Span-40 was 5:7:10.

Example 1: Nucleator Composition 1

The example was carried out by a process comprising the steps of:

adding 85 kg solid sorbitol and 45 kg chlorobenzaldehyde into a 2000 L reactor, adding about 600 L cyclohexane into the reactor, and stirring the mixture in the reactor for 30 minutes;

adding 10 kg composite catalyst 1 into the reactor and keeping the stirring, while heating the mixture for about half an hour for refluxing the solvent cyclohexane;

adding a solution containing 45 kg chlorobenzaldehyde and 200 L cyclohexane, and keeping stirring and heating for half an hour;

adding a solution containing 45 kg chlorobenzaldehyde and 200 L cyclohexane, and keeping the stirring and heating for 2.3 hours at the time when the volume of water generated in the condensation reaction and collected in the oil-water separator of the reactor reached 14 L;

cooling and reducing the pressure to recover the unreacted cyclohexane and water, and obtaining a crude product;

dispersing the crude product into water, adding 3 kg sodium hydroxide and stirring, and then adding 20 kg hydrogen peroxide with a concentration of about 30 wt % and stirring; and filter pressing, washing, and drying to obtain a white powder of the product, Nucleator composition 1.

By gas chromatography-mass spectrometry, the product, Nucleator composition 1, was found to contain 190.5 kg bis (p-chloro-benzylidene) sorbitol, 5.69 g tri (p-chloro-benzylidene) sorbitol, and 0.04 kg (p-chloro-benzylidene) sorbitol. The weight ratio of the ingredients is about 97.155:2.902:0.0204.

Example 2: Nucleator Composition 2

The example was carried out by a process comprising the steps of:

adding 85 kg solid sorbitol and 38.6 kg methylbenzaldehyde into a 2000 L reactor, adding 600 L cyclohexane into the reactor, and stirring the mixture in the reactor for 30 minutes;

adding 10 kg composite catalyst 2 into the reactor and keeping stirring, while heating the mixture for half an hour for the solvent cyclohexane to reflux;

adding a solution containing 38.6 kg methylbenzaldehyde and 200 L cyclohexane, and keeping stirring and heating for 0.5 hours;

adding a solution containing 38.6 kg methylbenzaldehyde and 200 L cyclohexane, and keeping stirring and heating for 2.4 hours at the time when the volume of water generated in the condensation reaction and collected in the oil-water separator of the reactor reached 15 L;

cooling and reducing the pressure to recover the unreacted cyclohexane and water, and obtaining a crude product;

dispersing the crude product into water, adding 3 kg sodium hydroxide and stirring, and adding 20 kg hydrogen peroxide with a concentration of about 30% wt and stirring; and filter pressing, washing, and drying, and then obtaining a white powder as a product, Nucleator composition 2.

By gas chromatography-mass spectrometry, the product, Nucleator composition 2, was found to contain 173.2 kg bis methyl benzylidene sorbitol, 0.35 g tri methyl benzylidene sorbitol, and 1.384 kg methyl benzylidene sorbitol, in a weight ratio of about 98.90:0.230:0.790.

Example 3: Nucleator Composition 3

The example was carried out by a process comprising the steps of:

adding 75 kg solid sorbitol and 37 kg dimethylbenzaldehyde into a 1000 L reactor, adding 250 L cyclohexane into the reactor, and stirring the mixture via a stirrer in the reactor while heating the reactor via an electric furnace to keep the reaction mixture at a temperature of 65° C.;

slowly adding 9.6 kg composite catalyst 3 in the reactor within about 10 minutes, and then keeping the reaction mixure at a constant temperature of 100~120° C. for half an hour;

adding 37 kg dimethylbenzaldehyde and 125 L cyclohexane into the reactor at the temperature for half an hour;

adding 37 kg dimethylbenzaldehyde and 125 L cyclohexane into the reactor and keeping the heating to continuously cycle and reflux cyclohexane in the reflux condenser and to remove the water generated by the aldol reaction for the continuous aldol reaction until the water generated reached 14.8 L;

cooling and reducing the pressure to recover the unreacted cyclohexane and water, and obtaining a crude product;

dispersing the crude product into water, adding 3 kg sodium hydroxide and stirring, and adding 20 kg hydrogen peroxide with a concentration of about 30% wt and stirring; and filter pressing, washing, and drying, and then obtaining a white powder as a product, Nucleator composition 3.

By gas chromatography-mass spectrometry, the product, Nucleator composition 3, was found to contain 169.1 kg bis (3,4-dimethyl benzylidene) sorbitol, 1.029 kg tri (3,4-dimethyl benzylidene) sorbitol, and 0.345 kg (3,4-dimethyl benzylidene) sorbitol, in a weight ratio of 99.177:0.604: 0.148.

Comparative Example 1: Comparative Nucleator Composition 1

Chemical synthesis was carried out in a 2000 L reactor equipped with a thermometer, a stirring paddle, an electric heating system for heating organic carrier, an oil-water separator and a reflux condenser by a process comprising the steps of:

adding 115 kg chlorobenzaldehyde and 70 kg solid sorbitol into the reactor, and adding 600 L solvent cyclohexane;

starting the stirring paddle, starting the electric heating system to maintain the temperature of the oil at 55° C. for about 30 minutes, so that chlorobenzaldehyde was fully dissolved in and mixed with the sorbitol;

slowly adding a composite catalyst containing 3.5 kg benzenesulfonic acid and 3.6 kg glycol ether in about 10 minutes and starting the chiller system; and resetting the oil temperature of the electric furnace at a constant temperature of 100-120° C. so that the cyclohexane continuously cycles and refluxes in the reflux condenser, and keeping the minimum azeotrope of cyclohexane and water generated by the aldol reaction flow through the reflux condenser for continuously removing water to carry out the reaction smoothly.

When the water removed reached a predetermined value, the reaction was completed and a crude product was obtained. The crude product then was transferred to a stainless steel barrel. Water was added in the stainless steel barrel.

After being dispersed in a dispersion machine and then treated with a colloid mill, the crude product was further leached and dehydrated in a centrifuge. The dehydrated crude product was transferred to a stainless steel barrel and 4 kg NaOH was added into the stainless steel barrel. After stirring rapidly until the mixture was turned into a slurry, 35 kg $H_2O_2$ (concentration of $H_2O_2$ is about 30%) was added. Then the process including stirring for 4 hours, washing and centrifugal dewatering was repeated two times. After drying and smashing, comparative nucleator composition 1 was obtained. By gas chromatography-mass spectrometry, the comparative nucleator composition 1 was found to contain no (p-chloro-benzylidene) sorbitol.

Comparative Example 2: Comparative Nucleator Composition 2

Chemical synthesis was carried out in a 2000 L reactor equipped with a thermometer, a stirring paddle, an electric heating system for heating organic carrier, an oil-water separator and a reflux condenser by a process comprising the steps of:

adding 120 kg methylbenzaldehyde and 85 kg solid sorbitol into the reactor, and adding 600 L solvent cyclohexane;

starting the stirring paddle, starting the electric heating system to maintain the temperature of the oil at 55° C. for about 30 minutes, so that methylbenzaldehyde was fully dissolved in and mixed with the sorbitol;

slowly adding composite catalyst containing 3.5 kg benzenesulfonic acid and 3.6 kg glycol ether in about 10 minutes and starting the chiller system;

resetting the oil temperature of the electric furnace at a constant temperature of 100-120° C. so that the cyclohexane continuously cycles and refluxes in the reflux condenser, and keeping the minimum azeotrope of cyclohexane and water generated by the aldol reaction flow through the reflux condenser for continuously removing water to carry out the reaction smoothly.

When the water removed reached a predetermined value, the reaction was completed and a crude product was obtained. The crude product then was transferred to a stainless steel barrel. Water was added in the stainless steel barrel.

After being dispersed in a dispersion machine and then treated with a colloid mill, the crude product was further leached and dehydrated in a centrifuge. The dehydrated crude product was transferred to a stainless steel barrel and 4 kg NaOH was added in the stainless steel barrel. After stirring rapidly for 4 hours until the mixture was turned into a slurry, 35 kg $H_2O_2$ (concentration of $H_2O_2$ is about 30%) was added. Then the process including stirring for 4 hours, washing and centrifugal dewatering was repeated two times. After drying and smashing, comparative nucleator composition 2 was obtained. By gas chromatography-mass spectrometry, the comparative nucleator composition 2 was found to contain no trimethyl benzylidene sorbitol.

Comparative Example 3: Comparative Nucleator Composition 3

Chemical synthesis was carried out in a 1000 L reactor equipped with a thermometer, a stirring paddle, an electric heating system for heating organic carrier, an oil-water separator and a reflux condenser by a process comprising the steps of:

adding 108 kg dimethylbenzaldehyde and 73 kg solid sorbitol into the reactor, and adding 450 L solvent cyclohexane;

starting the stirring paddle, starting the electric heating system to maintain the temperature of the oil at 55° C., so that dimethylbenzaldehyde was fully dissolved in and mixed with the sorbitol;

slowly adding 8.3 kg composite catalyst containing benzenesulfonic acid, ethylene glycol monomethyl ether and Span-60 in about 10 minutes and starting the chiller system;

resetting the oil temperature of the electric furnace at a constant temperature of 100-120° C. so that the cyclohexane continuously cycles and refluxes in the reflux condenser, and keeping the minimum azeotrope of cyclohexane and water generated by the aldol reaction flow through the reflux condenser for continuously removing water to carry out the reaction smoothly.

When the water removed reached a predetermined value, the reaction was completed and a crude product was obtained. The reaction lasted for about 1.5-2.0 hours. After the solvent was recovered and the synthesis reaction was completed, the oil was reset at 55° C. In this case, the residual heat was used to distill and recover solvent cyclohexane. When the amount of the solvent distilled began to reduce, a vacuum system was started to reduce the pressure until the cyclohexane was completely distilled and then comparative nucleator composition 3 was obtained in the reactor. By gas chromatography-mass spectrometry, the comparative nucleator composition 3 was found to contain no (3,4-dimethyl benzylidene) sorbitol.

The method for analyzing each of the products in Examples 1-3 and Comparative Examples 1-3 via gas chromatography—mass spectrometry comprised the steps of:

weighing approximately 0.5000 g of each of the products in a 10.0 ml flask;

dissolving the product in dimethyl sulfoxide solvent under ultrasound; and determining all of the components by GCMS area normalization method, wherein the chromatogram did not compare integral raw material impurities (3,4-dimethyl benzaldehyde).

According to the experimental analysis, the sample remaining in the system was large. After injection, triacetal was detected in the first blank. The second blank spectra was clean. Therefore, the residual was removed by a system blank program between each sample. Each sample was analyzed twice, and the second analysis data were selected for analysis. The measurement results were automatically calculated by the GCMS solution 4.11 SU1 software.

The gas chromatography conditions used were detailed as follows,
   inlet temperature=300° C.;
   inlet time=0.5 minutes'
   oven temperature=120° C.;
   pressure=91.0 kPa;
   total flow=6.0 ml/min;
   column flow rate=3.00 ml/min;
   line speed=65.0 cm/sec; and
   purge flow rate=3 ml/min.

The temperature program included maintaining the temperature at 120° C. for 1.00 min, raising the temperature to 300° C. at a heating rate of 15° C./min, and maintaining the temperature at 300° C. for 17.00 min.

The MS conditions are detailed as follows,
   ion source temperature=260° C.;
   interface temperature=300° C.;
   scanning speed=2000 amu/s;
   scanning range=m/z80 m/z1000;
   solvent delay=1.50 min;
   capture start time=1.75 min; and
   capture end time=30.00 min.

EXPERIMENTAL EXAMPLES

Effects of the nucleator compositions of Examples 1-3 on the performances of polypropylene (PP) and polyethylene (PE) were determined.

Each of the nucleator compositions made by the methods of Examples 1-3 and Comparative Examples 1-3 was added into PP and PE individually for analyzing any effects of the nucleator compositions of Examples 1-3 on the performances of PP and PE.

1.5 g~2.5 g of each of the nucleator compositions was added to 1000 g PP or PE resin, and the extrusion temperature was 180~210° C. In order to test effects of the nucleator compositions on the PP or PE articles, in all of the examples, the concentration of each of the nucleator compositions in the articles was 0.15~0.25% (relative to the mass of the PP and PE resin), and the extrusion temperature was 180~210° C.

2 g of each of the nucleator compositions according to Examples 1-3 and Comparative Examples 1-3 was added into 1000 g resin and mixed by a high speed mixer for 5 minutes to obtain a resin mixture. The resin mixture was squeezed by a twin screws extruder at the extrusion temperature of 180~210° C. to obtain samples individually.

Similarly, according to the method mentioned above, homo-polymer polypropylene resin composition HP500N having nonnucleator and linear low density polyethylene resin composition 7042 having no nucleator was prepared and extruded by a twin screw extruder to obtain comparative samples.

The PP composition was injection molded at 230° C. to obtain samples for light transmittance and haze test and for impact test. The PE composition was extruded to blow a film at 200° C. to obtain samples for light transmittance and haze test. The PE composition was injection molded at 200° C. to obtain samples for impact test. The thickness of PP samples for light transmittance and haze test was 1.0 mm. The thickness of PE samples for light transmittance and haze test was 0.030 mm.

The table 1 shows the effects of the nucleator compositions according to Examples of the present invention on the performances and processing temperature of PE and PP.

TABLE 1

Effects of nucleator compositions on the performance of injection molded samples (weight content of nucleator in the polymer is 0.2%)

| Polymer | Nucleator composition | Generation of nucleator | Light transmittance % | Haze % | Best extrusion temperature ° C. |
|---|---|---|---|---|---|
| PE | Example 1 | Second generation | 91.2 | 3.6 | 172 |
| PE | Example 2 | Second generation | 92.1 | 3.3 | 174 |
| PE | Example 3 | Third generation | 94.3 | 3.5 | 169 |
| PE | Comparative Example 1 | Second generation | 87.1 | 4.7 | 178 |
| PE | Comparative Example 2 | Second generation | 85.2 | 4.6 | 176 |
| PE | Comparative Example 3 | Third generation | 86.7 | 4.8 | 178 |
| PE | No nucleator | — | 84.7 | 13.5 | 190 |
| PP | Example 1 | Second generation | 90.2 | 15.4 | 195 |
| PP | Example 2 | Second generation | 91.8 | 15.3 | 198 |
| PP | Example 3 | Third generation | 89.6 | 15.0 | 195 |
| PP | Comparative Example 1 | Second generation | 84.3 | 17.1 | 208 |
| PP | Comparative Example 2 | Second generation | 86.0 | 17.3 | 205 |

TABLE 1-continued

Effects of nucleator compositions on the performance of injection molded samples (weight content of nucleator in the polymer is 0.2%)

| Polymer | Nucleator composition | Generation of nucleator | Light transmittance % | Haze % | Best extrusion temperature ° C. |
|---|---|---|---|---|---|
| PP | Comparative Example 3 | Third generation | 86.3 | 17.7 | 208 |
| PP | No nucleator | — | 80.8 | 48.6 | 210 |

According to the results shown above, the nucleator compositions according to Examples 1-3 of the present invention can be used to prepare polyolefin with improved transparency.

Compared with PE prepared by the nucleator having no sorbitol diacetal or sorbitol triacetal, the PE prepared by the nucleator composition of the invention having sorbitol acetal and sorbitol triacetal was much more transparent. And the results from the light transmittance and haze test also showed that the PE prepared by the nucleator composition of the invention having sorbitol acetal and sorbitol triacetal was better.

Compared with PP prepared by nucleator having no sorbitol diacetal or sorbitol triacetal, the PP prepared by the nucleator composition of the invention having sorbitol acetal and sorbitol triacetal was much more transparent. And the results from light transmittance and haze test also showed that the PP prepared by the nucleator composition having sorbitol acetal and sorbitol triacetal was better.

With regard to the temperature in the process, i.e. extrusion temperature, compared with PE and PP containing commercially available nucleator products which contained no sorbitol triacetal and were prepared in the same experimental conditions as those of Examples 1-3 and Comparative Examples 1-3, the PE and PP containing the nucleator composition according to Examples 1-3 of the present invention had more desirable performances and had lower extrusion temperature, for instance 10-20° C. lower. The effects of commercially available nucleators on injection mold samples are shown in Table 2.

TABLE 2

Effects of commercially available nucleators on performances of injection molded samples (weight content of nucleator in the polymer is 0.2%)

| Polymer | Nucleator composition | Light transmittance % | Haze % | Best extrusion temperature ° C. |
|---|---|---|---|---|
| PE | Commercially available product | 88.5 | 4.6 | 188 |
| PP | Commercially available product | 87.8 | 16.5 | 207 |

The commercially available nucleator products in Table 2 contained no sorbitol triacetal and were purchased.

The invention claimed is:

1. A nucleator composition, comprising a compound represented by formula (I), a compound represented by formula (II), a compound represented by formula (III), and a compound represented by formula (IV),

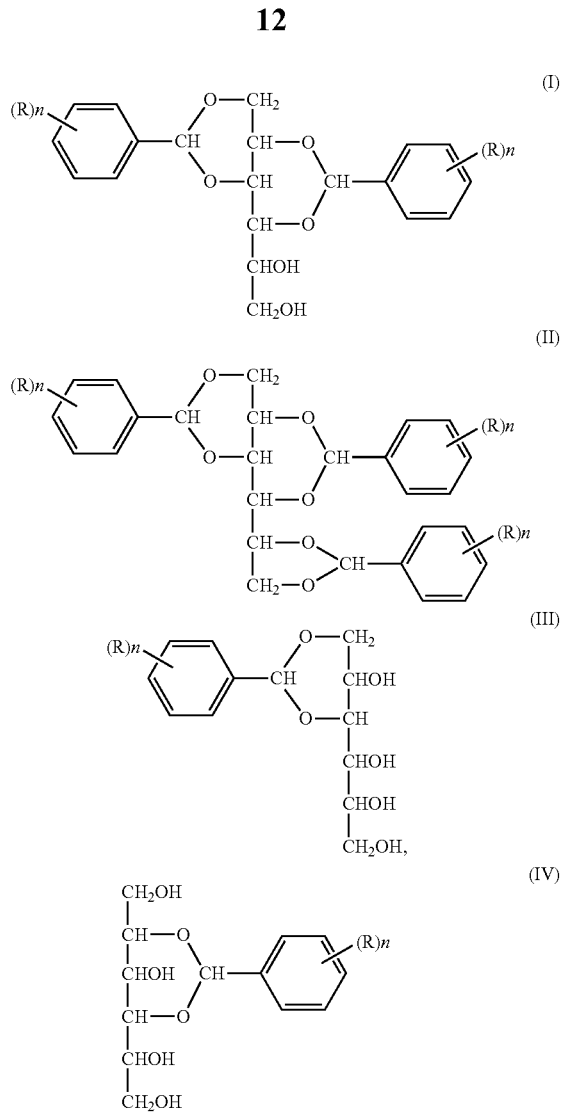

wherein each of the n in formulae (I), (II), (III) and (IV) is independently 1 or 2;
each of the R in formulae (I), (II), (III) and (IV) is independently selected from $C_1$-$C_8$ alkyl, $C_1$-$C_4$ alkoxy, carboxy, hydroxyl, halogen, and $C_1$-$C_6$ alkylthio;
and the ratio of the weight of the compound represented by formula (I), the weight of the compound represented by formula (II), and the combined weight of the compounds represented by formula (III) and formula (IV) is (97.00-99.90):(0.20-8.00):(0.02-1.00).

2. The nucleator composition according to claim 1, wherein R is —Cl, —Br, —$CH_3$ or —$CH_2$—$CH_3$.

3. A method for preparing the nucleator composition according to claim 1, comprising the steps of:
1) mixing ⅓ by weight of an aromatic aldehyde needed and all sorbitol in a vessel by stirring to form a mixture;
2) adding cyclohexane to the mixture of step 1);
3) adding a composite catalyst to the product of step 2);
4) heating the product of step 3) for cyclohexane refluxing to carry out dehydration condensation reaction, then continuous heating for 0.4-1.0 hour;
5) adding cyclohexane and ⅓ by weight of the aromatic aldehyde needed to the product of step 4);
6) heating the product of step 5) for 0.4-1 hour to form a heated mixture;

7) adding cyclohexane and ⅓ by weight of the aromatic aldehyde needed to the heated mixture, and keeping heating until the mole ratio of water to sorbitol collected in an oil-water separator is 1.5-2:1;
8) lowering the temperature, reducing the pressure inside the vessel and recovering cyclohexane and water via distillation, and then obtaining a crude product;
9) dispersing the crude product into water, adding sodium hydroxide and hydrogen peroxide, and stirring; and
10) filter pressing, washing, and drying, and then obtaining a white powder of the nucleator composition,
wherein the aromatic aldehyde is represented by the following formula

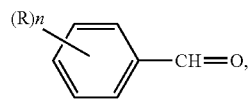

wherein n is 1 or 2, and R is selected from $C_1$-$C_8$ alkyl, $C_1$-$C_4$ alkoxy, carboxy, hydroxyl, halogen, or $C_1$-$C_6$ alkylthio,
and the composite catalyst comprises a mixture of toluene-p-sulfonic acid and glycol ether.

4. The method according to claim 3, wherein the glycol ether is selected from the group consisting of ethylene glycol monomethyl ether, ethylene glycol dimethyl ether, ethylene glycol diethyl ether, ethylene glycol monobutyl ether and ethylene glycol di-butyl ether, and the mole ratio of toluene-p-sulfonic acid to glycol ether is 3-5:8-10.

5. The method according to claim 3, wherein the volume ratio of cyclohexane added in step 5) to cyclohexane in step 1) is 1:3, the volume ratio of cyclohexane added in step 7) to cyclohexane in step 1) is 1:3, and the weight of cyclohexane added in step 5) is equal to the weight of cyclohexane added in step 7).

6. Use of the nucleator composition according to claim 1 in the preparation of a polymer with improved performance comprising the nucleator composition of claim 1, wherein the performance is improved compared with a corresponding polymer without the nucleator composition of claim 1, wherein the polymer with improved performance is polyethylene or polypropylene with improved performance, and
wherein when the polymer with improved performance is a polyethylene with improved performance, the improved performance is selected from the group consisting of (a) reduction of extrusion temperature compared with an extrusion temperature of a corresponding polyethylene without the nucleator composition of claim 1, (b) increase of transparency compared with transparency of a corresponding polyethylene without the nucleator composition of claim 1, (c) increase of glossiness compared with glossiness of a corresponding polyethylene without the nucleator composition of claim 1, (d) improvement of flexural modulus compared with flexural modulus of a corresponding polyethylene without the nucleator composition of claim 1, (e) improvement of tensile strength compared with tensile strength of a corresponding polyethylene without the nucleator composition of claim 1, (f) improvement of heat distortion temperature compared with a heat distortion temperature of a corresponding polyethylene without the nucleator composition of claim 1, (g) improvement of dimensional stability compared with dimensional stability of a corresponding polyethylene without the nucleator composition of claim 1, (h) reduction of the number of molding cycle compared with the number of molding cycle of a corresponding polyethylene without the nucleator composition of claim 1, and (i) improvement of polymer production efficiency compared with polymer production efficiency of a corresponding polyethylene without the nucleator composition of claim 1; and
wherein when the polymer with improved performance is a polypropylene with improved performance, the improved performance is selected from the group consisting of (a) reduction of extrusion temperature compared with an extrusion temperature of a corresponding polypropylene without the nucleator composition of claim 1, (b) increase of transparency compared with transparency of a corresponding polypropylene without the nucleator composition of claim 1, (c) increase of glossiness compared with glossiness of a corresponding polypropylene without the nucleator composition of claim 1, (d) improvement of flexural modulus compared with flexural modulus of a corresponding polypropylene without the nucleator composition of claim 1, (e) improvement of tensile strength compared with tensile strength of a corresponding polypropylene without the nucleator composition of claim 1, (f) improvement of heat distortion temperature compared with a heat distortion temperature of a corresponding polypropylene without the nucleator composition of claim 1, (g) improvement of dimensional stability compared with dimensional stability of a corresponding polypropylene without the nucleator composition of claim 1, (h) reduction of the number of molding cycle compared with the number of molding cycle of a corresponding polypropylene without the nucleator composition of claim 1, and (i) improvement of polymer production efficiency compared with polymer production efficiency of a corresponding polypropylene without the nucleator composition of claim 1.

7. Use of the nucleator composition according to claim 1 in the preparation of a polymer with improved transparency and reduced extrusion temperature, wherein the transparency is improved compared with transparency of a corresponding polymer without the nucleator composition of claim 1 and the extrusion temperature is reduced compared with extrusion temperature of the corresponding polymer without the nucleator composition of claim 1.

8. A polymer composition comprising a polymer and the nucleator composition according to claim 1, wherein the weight content of the nucleator composition in the polymer composition is 0.03-0.3%.

9. The polymer composition according to claim 8, wherein the polymer is polyethylene or polypropylene.

10. The polymer composition according to claim 9, wherein the polyethylene is selected from the group consisting of low density polyethylene, medium density polyethylene, high density polyethylene, linear low density polyethylene, ultrahigh molecular weight polyethylene and ethylene copolymer, and wherein the polypropylene is selected from the group consisting of isotactic polypropylene, random polypropylene, syndiotactic polypropylene, chlorinated polypropylene and grafted polypropylene.

11. The use according to claim 6, wherein the polymer is in the form of a polymer film, polymer sheet, polymer molding article or polymer article.

12. The use according to claim 6, wherein the polymer is in the form of a polymer film, polymer sheet, or polymer molding article and the improved performance is increased flexural modulus and tensile strength of the polymer film, polymer sheet, or polymer molding article compared with flexural modulus and tensile strength of a corresponding polymer film, polymer sheet, or polymer molding article without the nucleator composition.

13. The use according to claim 6, wherein the polymer is in the form of a polymer article, and the improved performance is increased heat distortion temperature and/or improved dimensional stability compared with a heat distortion temperature and/or dimensional stability of a corresponding polymer article without the nucleator composition.

14. A method of preparing an improved polymer, comprising adding the nucleator composition according to claim 1 to a starting polymer without the nucleator composition to obtain the improved polymer, wherein the improved polymer is improved compared with the starting polymer without the nucleator composition, wherein the starting polymer is a polyethylene or polypropylene without the nucleator composition, and wherein when the starting polymer is a polyethylene without the nucleator composition, the improved polymer has at least one improved performance selected from the group consisting of (a) reduced extrusion temperature compared with an extrusion temperature of the starting polyethylene without the nucleator composition, (b) increased transparency compared with transparency of the starting polyethylene without the nucleator composition, (c) increased glossiness compared with glossiness of the starting polyethylene without the nucleator composition, (d) increased flexural modulus compared with flexural modulus of the starting polyethylene without the nucleator composition, (e) increased tensile strength compared with tensile strength of the starting polyethylene without the nucleator composition, (f) improvement of heat distortion temperature compared with a heat distortion temperature of the starting polyethylene without the nucleator composition, (g) improvement of dimensional stability compared with dimensional stability of the starting polyethylene without the nucleator composition, (h) reduction of the number of molding cycle compared with the number of molding cycle of the starting polyethylene without the nucleator composition, and (i) increased polymer production efficiency compared with polymer production efficiency of the starting polyethylene without the nucleator composition; and wherein when the starting polymer is a polypropylene without the nucleator composition, the improved polymer has at least one improved performance selected from the group consisting of (a) reduced extrusion temperature compared with an extrusion temperature of the starting polypropylene without the nucleator composition, (b) increased transparency compared with transparency of the starting polypropylene without the nucleator composition, (c) increased glossiness compared with glossiness of the starting polypropylene without the nucleator composition, (d) increased flexural modulus compared with flexural modulus of the starting polypropylene without the nucleator composition, (e) increased tensile strength compared with tensile strength of the starting polypropylene without the nucleator composition, (f) improvement of heat distortion temperature compared with a heat distortion temperature of the starting polypropylene without the nucleator composition, (g) improvement of dimensional stability compared with dimensional stability of the starting polypropylene without the nucleator composition, (h) reduction of the number of molding cycle compared with the number of molding cycle of the starting polypropylene without the nucleator composition, and (i) increased polymer production efficiency compared with polymer production efficiency of the starting polypropylene without the nucleator composition.

15. The method according to claim 14, wherein the improved performance is increased transparency and/or reduced extrusion temperature compared with the transparency and/or extrusion temperature of the starting polymer without the nucleator composition.

16. The method according to claim 14, wherein the improved polymer is in the form of a polymer film, polymer sheet, polymer molding article or polymer article.

17. The method according to claim 14, wherein the improved polymer is in the form of a polymer film, polymer sheet, or polymer molding article, and the improved performance is increased flexural modulus and/or tensile strength compared with flexural modulus and/or tensile strength of the polymer film, polymer sheet, or polymer molding article without the nucleator composition.

18. The method according to claim 14, wherein the improved polymer is in the form of a polymer article, and the improved performance is increased heat distortion temperature and/or improved dimensional stability compared with a heat distortion temperature and/or dimensional stability of the starting polymer without the nucleator composition in the form of a polymer article.

19. The method according to claim 3, wherein R is —Cl, —Br, —CH$_3$ or —CH$_2$—CH$_3$.

20. The use of the nucleator composition according to claim 6, wherein R is —Cl, —Br, —CH$_3$ or —CH$_2$—CH$_3$.

21. The use of the nucleator composition according to claim 7, wherein R is —Cl, —Br, —CH$_3$ or —CH$_2$—CH$_3$.

22. The nucleator composition according to claim 8, wherein R is —Cl, —Br, —CH$_3$ or —CH$_2$—CH$_3$.

23. The method according to claim 14, wherein R is —Cl, —Br, —CH$_3$ or —CH$_2$—CH$_3$.

24. The method according to claim 15, wherein R is —Cl, —Br, —CH$_3$ or —CH$_2$—CH$_3$.

25. The method according to claim 16, wherein R is —Cl, —Br, —CH$_3$ or —CH$_2$—CH$_3$.

26. The method according to claim 17, wherein R is —Cl, —Br, —CH$_3$ or —CH$_2$—CH$_3$.

27. The method according to claim 18, wherein R is —Cl, —Br, —CH$_3$ or —CH$_2$—CH$_3$.

28. The polymer composition of claim 8, wherein the weight content of the nucleator composition in the polymer composition is 0.05-0.25%.

29. The polymer composition of claim 10, wherein the ethylene copolymer is selected from the group consisting of ethylene-propylene copolymer, EVA, ethylene-butene copolymer, ethylene-octene copolymer and ethylene unsaturated ester copolymer.

* * * * *